(12) United States Patent
Kamousi et al.

(10) Patent No.: US 8,204,581 B2
(45) Date of Patent: Jun. 19, 2012

(54) METHOD TO DISCRIMINATE ARRHYTHMIAS IN CARDIAC RHYTHM MANAGEMENT DEVICES

(75) Inventors: Baharan Kamousi, Sunnyvale, CA (US); Bryant Lin, Menlo Park, CA (US); Paul J Wang, Saratoga, CA (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 105 days.

(21) Appl. No.: 12/340,772

(22) Filed: Dec. 22, 2008

(65) Prior Publication Data
US 2010/0174206 A1 Jul. 8, 2010

Related U.S. Application Data

(60) Provisional application No. 61/010,147, filed on Jan. 3, 2008.

(51) Int. Cl.
*A61B 5/02* (2006.01)
*A61N 1/00* (2006.01)

(52) U.S. Cl. .................. 600/518; 600/515; 607/5
(58) Field of Classification Search .......... 600/508–528; 607/4–5, 9, 14
See application file for complete search history.

(56) References Cited

U.S. PATENT DOCUMENTS

| 2004/0127945 A1* | 7/2004 | Collins et al. | 607/5 |
| 2006/0161069 A1* | 7/2006 | Li | 600/515 |
| 2007/0197928 A1* | 8/2007 | Kim et al. | 600/515 |
| 2008/0175446 A1* | 7/2008 | Kirby et al. | 382/118 |
| 2010/0217144 A1* | 8/2010 | Brian | 600/523 |

* cited by examiner

*Primary Examiner* — Niketa Patel
*Assistant Examiner* — Catherine Voorhees
(74) *Attorney, Agent, or Firm* — Evans & Molinelli PLLC; Eugene J. Molinelli

(57) ABSTRACT

Techniques for discrimination of heart rhythms in cardiac rhythm management devices include determining a current covariance matrix of multiple electrograms measuring each current heart beat, determining a distance measure between the current covariance matrix and a predetermined covariance matrix of the multiple electrograms measuring at least one different heart beat; and determining whether the heart beat represents ventricular tachycardia based on the distance measure.

8 Claims, 7 Drawing Sheets

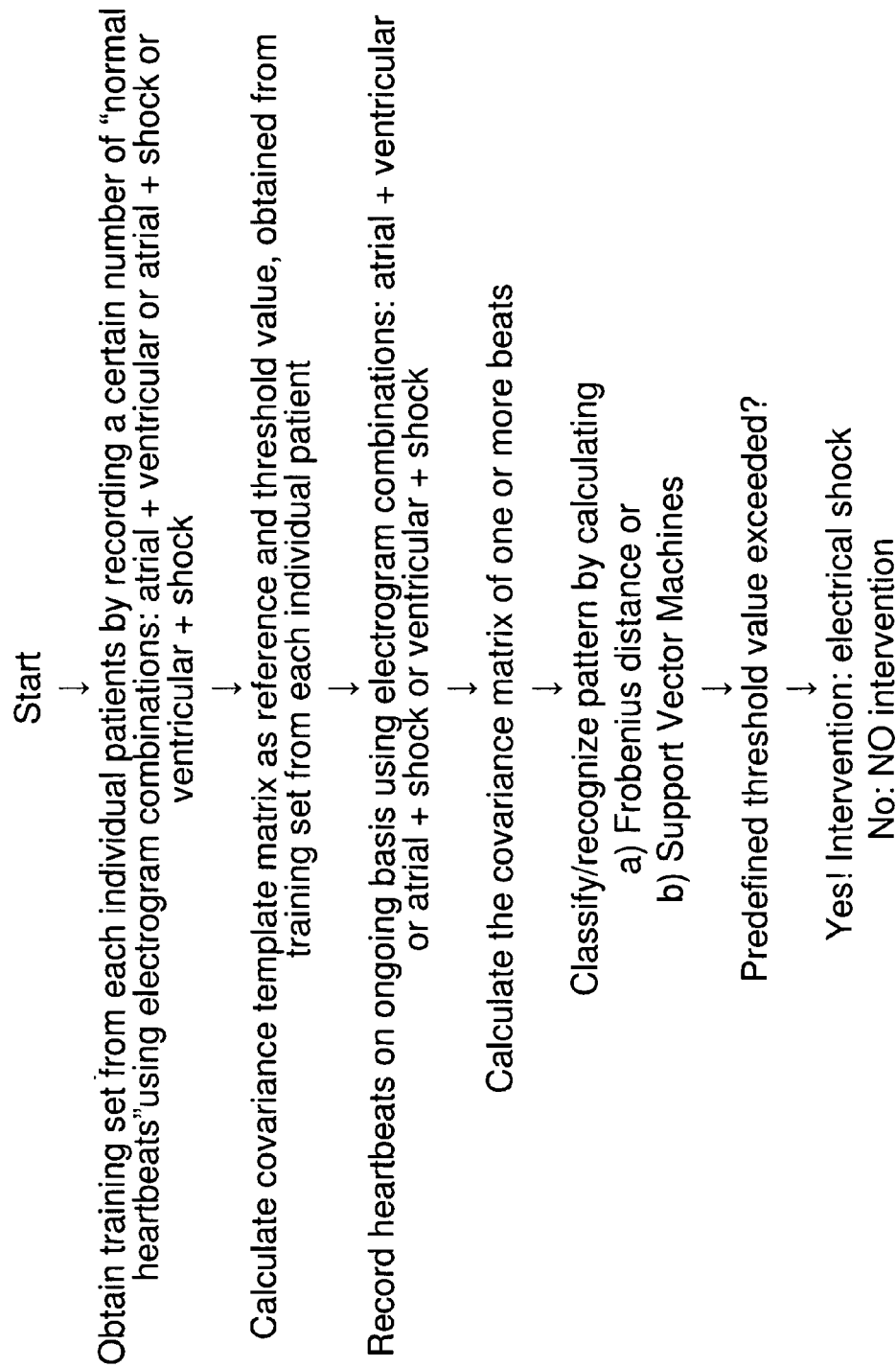

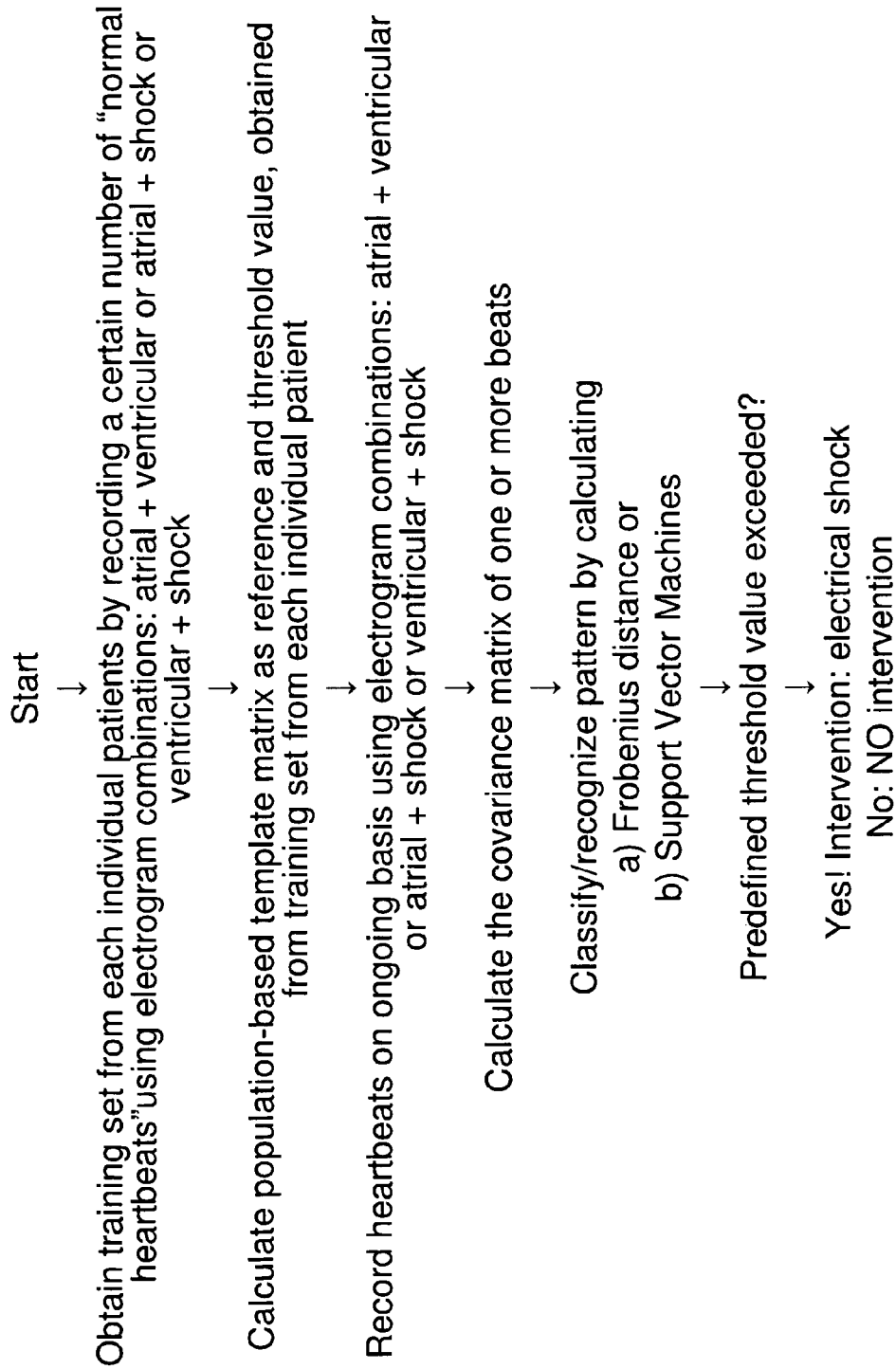
Figure 6: Flow chart summarizing steps included in a method for discriminating supraventricular tachycardia from ventricular tachycardia/ventricular fibrillation using population-based template matrices and Frobenius distance or support vector machines for pattern classification/recognition

METHOD TO DISCRIMINATE ARRHYTHMIAS IN CARDIAC RHYTHM MANAGEMENT DEVICES

RELATED APPLICATION

This application claims priority and other benefits from U.S. Provisional Patent Application Ser. No. 61/010,147, filed Jan. 3, 2008, entitled "Method to discriminate arrhythmias in implantable devices".

FIELD OF INVENTION

This invention pertains to methods for treating cardiac arrhythmias in cardiac rhythm management devices. In particular, the present invention deals with discriminating between different types of tachyarrhythmias.

BACKGROUND

The normal rhythmic impulse of the heart is first generated in the sinoatrial (SA) node, which is the normal pacemaker of the heart, typically initiating 60-100 heartbeats per minute. The impulse is then spread throughout the atria causing atrial contraction, and is then conducted to the atrioventricular (AV) node where the impulse passes into the ventricles. The ventricles of a normal heart are then electrically stimulated by excitation emanating from the AV node that spreads via specialized conduction pathways.

If the heart's rhythm deviates from the normal pace, either bradycardia (bradyarrhythmia) or tachycardia (tachyarrhythmia) result. In case of bradycardia, the heart beats less than 60 times per minute and becomes unable to maintain adequate circulation; this condition is usually rectified with medical treatment. In case of tachycardia, the heart becomes faster than 100 beats per minute and may start to beat irregular and uncoordinated and escalate into a fibrillation event, eventually leading to cardiac inefficiency and a possibly life-threatening event. Termination of a tachycardia is commonly referred to as cardioversion.

Examples of tachyarrhythmias include sinus tachycardia, atrial tachycardia, atrial fibrillation, ventricular tachycardia and ventricular fibrillation. The most dangerous tachyarrhythmias are those that have their origin in the ventricles, namely ventricular tachycardia (VT) and ventricular fibrillation (VF). Sinus tachycardia, atrial tachycardia, atrial fibrillation all originate from the upper chambers of the heart, the atria, they are collectively referred to as supraventricular tachycardia (SVT).

VT occurs in the lower chambers of the heart, the ventricles, and leads, without immediate treatment, to ventricular fibrillation (VF), which presents itself as uncoordinated and inefficient contractions of the ventricles that quickly lead to hypoxia, cardiac tissue damage, cardiac arrest and sudden death, if not treated quickly. Therefore, ventricular tachycardia requires immediate correction of the heartbeat.

SVT causes atrial fibrillation and flutter, and often results in chest pain, fatigue and dizziness. However, unlike VT, SVT is generally not a life-threatening condition and, therefore, does typically not require immediate correction of the heartbeat.

Implantable cardioverter defibrillators (ICDs) are small battery-powered cardiac rhythm management devices that are designed to treat ventricular tachyarrhythmias by delivering an electrical shock pulse to the heart. ICDs typically consist of a pulse generator connected to one or two insulated wires or leads. The pulse generator is usually implanted under the collarbone, just beneath the skin. The main lead is inserted into the lower right heart chamber (the right ventricle). A second lead may be placed in the upper right heart chamber (the right atrium). These devices constantly monitor the rate and rhythm of the heart, sense the heart rhythm and classify the rhythm according to an arrhythmia detection scheme in order to detect episodes of tachycardia or fibrillation. Upon detecting an arrhythmia, the ICD delivers a generally painful electrical shock therapy to reset the heart to a normal sinus rhythm. Inappropriately delivered therapies can induce arrhythmias (proarrhythmia) or worsen existing arrhythmias in patients.

Since VT requires immediate correction of the heartbeat, while SVT does not, it is important to distinguish between the two types of tachycardia. Many different rhythm discrimination algorithms have been proposed to distinguish between VT and SVT. These algorithms utilize various information such as rate, onset, stability and morphology differences to discriminate different rhythms from each other {Lee et al. (2005), Pacing Clin Electrophysiol 28, pp. 1032-1040; Gollob et al. (2001), Chest 119, pp. 1210-1221; Aliot et al. (2004), Europace 6, pp. 273-286; Stadler et al. (2003), Pacing and Clinical Electrophysiology 26 (5), pp. 1189-1201; Gold et al. (2002), J Cardiovasc Electrophysiol 13, pp. 1092-1097; Klein et al. (2006), J Cardiovasc Electrophysiol 17, pp. 1310-1319; Anselme et al. (2007), Pacing and Clinical Electrophysiology 30 (s1), pp. S128-S133}.

Rate discrimination evaluates the rate of the lower chambers of the heart (the ventricles) and compares it to the rate in the upper chambers of the heart (the atria). If the rate in the atria is faster than or equal to the rate in the ventricles, then the rhythm is most likely not ventricular in origin, and is usually more benign. If this is the case, the ICD does not provide any therapy. Morphology discrimination checks the morphology of every ventricular beat and compares it to what the ICD believes is a normally conducted ventricular impulse for the patient. This normal ventricular impulse is often an average of a multiple of beats of the patient taken in the recent past.

Besides development of different algorithms, second generation ICDs were introduced which utilize dual chamber pacing and arrhythmia detection, compared to the single chamber-first generation ICDs {Lavergne et al. (1997), Pacing Clin Electrophysiol 20, pp. 182-8}. Table 1 shows advantages and disadvantages of each criterion of arrhythmia detection algorithms in single-chamber versus dual-chamber ICDs.

TABLE 1

{taken from Aliot et al. (2004), Europace 6, pp. 273-286}

| Criteria | Strong points | Weak points linked to the algorithm itself or to pacing/sensing uncertainties |
|---|---|---|
| Single chamber | | |
| Ventricular stability | Discriminates AF from VT | Organized SVT vs VT, false negatives (unstable VT) |
| Ventricular onset | Discriminates ST from VT | SVT vs VT |

TABLE 1-continued

{taken from Aliot et al. (2004), Europace 6, pp. 273-286}

| Criteria | Strong points | Weak points linked to the algorithm itself or to pacing/sensing uncertainties |
|---|---|---|
| R-wave morphology | VT vs SVT/ST | BBB, artifacts, body motion, exercise (for temporal analysis) |
| Dual chamber | | |
| Atrial stability | AF vs organized SVT | Oversensing, undersensing (refractory periods) |
| Atrial vs ventricular rates/intervals | SVT vs dissociated VT | Tachycardia with 1/1 AV or VA conduction, dual-tachycardia, oversensing, undersensing |
| Chamber of origin | 1/1 conducting SVT vs VT | A oversensing, undersensing |
| AV association | SVT/ST vs dissociated VT | Tachycardia with 1/1 AV or VA conduction, oversensing, undersensing |
| P:R pattern | SVT vs dissociated VT | Tachycardia with 1/1 AV or VA conduction, oversensing, undersensing |
| PVS | 1/1 SVT/ST vs VT | No ventricular capture |

BBB = bundle-branch block;
ST = sinus tachycardia;
SVT = supraventricular tachycardia;
VT = ventricular tachycardia;
PVS = premature ventricular stimulus;
AF = atrial fibrillation;
AV = atrioventricular;
VA = ventriculoatrial.

However, despite the described efforts to refine the detection and treatment of ventricular tachycardia, lack of specificity of VT detection has to date remained a significant shortcoming of current ICDs. Furthermore, many of the present methods are computationally very complex and may be beyond the capacity that a small battery-powered device can handle.

As a consequence, still up to 40% of arrhythmic patients suffer daily from unnecessary administration of painful shocks that lead to depression, anxiety and an overall reduction of the quality of life. Furthermore, the inappropriate administration of electric shocks may make patients prone to proarrhythmias and so increase the frequency of arrythmias or even provoke new ones.

It is apparent from the current situation that there is still a great need for an algorithm that accurately and specifically distinguishes ventricular from supraventricular tachycardias and that has improved, less complex computational power.

SUMMARY

The present invention relates to an algorithm that can be implemented in a cardiac rhythm management device for tachycardia detection and for discrimination between ventricular tachycardia and supraventricular tachycardia with high specificity and high sensitivity. Advantageously, the described algorithm is less computationally complex and faster than currently implemented, less accurate methods for arrhythmia discrimination.

The following summary is not intended to include all features and aspects of the present invention nor does it imply that the invention must include all features and aspects discussed in this summary.

Embodiments of the invention describe a novel, highly accurate and easy to implement, covariance-based algorithm for precise ICD rhythm classification to reduce the likelihood of false positive or false negative arrhythmia detection. The algorithm is applicable on both single-chamber and dual-chamber ICDs. Ventricular tachycardia (VT) is distinguished from supraventricular tachycardia (SVT) with high specificity and high sensitivity by estimating and comparing the covariance matrices of the different heart rhythms utilizing intracardiac and/or extracardiac signals. This algorithm leads to improved detection specificity and improved detection sensitivity and, thus, accomplishes to avoid unnecessary administration of painful electrical shocks.

DRAWINGS

The accompanying drawings, which are not necessarily to scale, illustrate embodiments of the invention and, together with the description, serve to explain the invention. These drawings are offered by way of illustration and not by way of limitation. Those skilled in the art will recognize that many of the examples provided have suitable alternatives that may be utilized.

Figure 3:
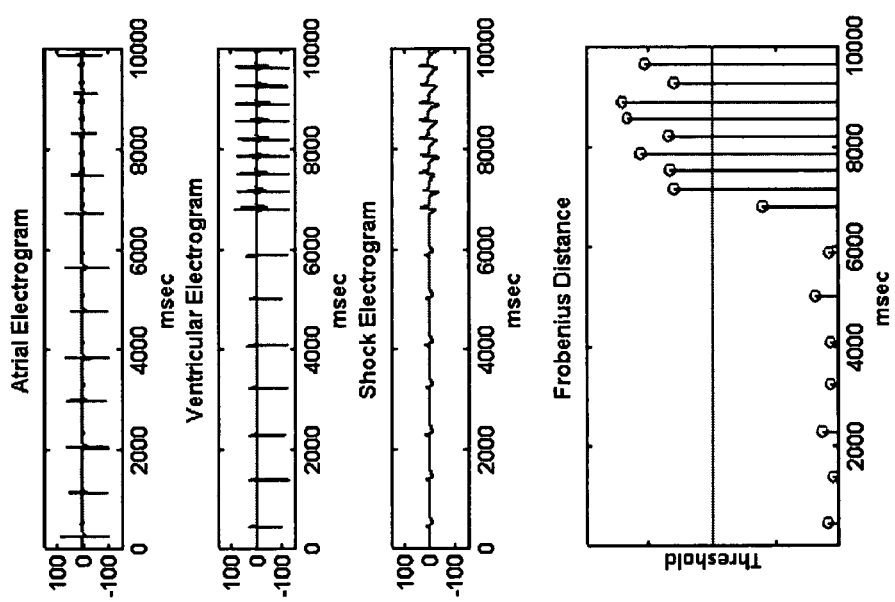

FIG. 3 depicts an example of a ventricular tachycardia (VT) episode. The top three graphs show atrial, ventricular and shock electrograms. The bottom graph displays Frobenius distances of each beat from the template. Beats with distances above the threshold level are classified as VT.

Figure 4:
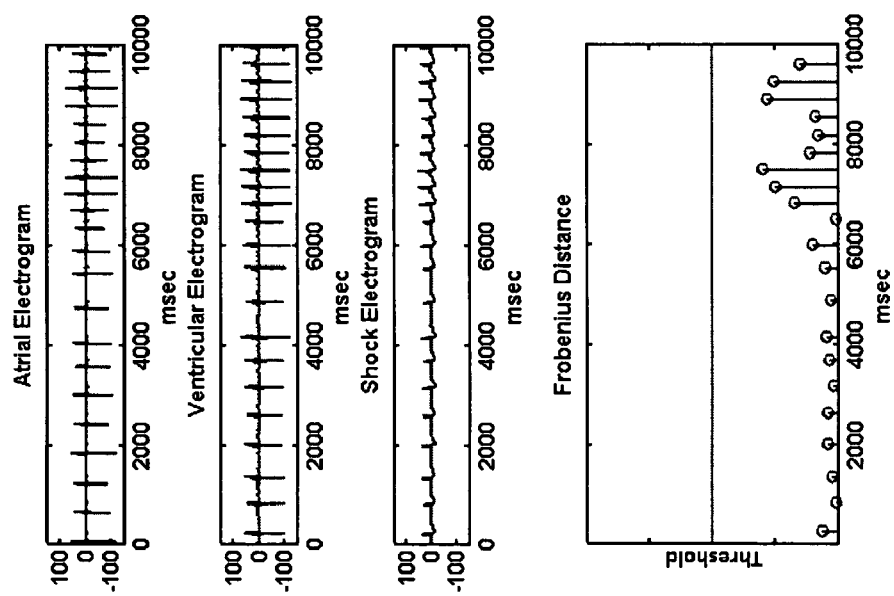

FIG. 4 depicts an example of a supraventricular tachycardia (SVT) episode. The top three graphs show atrial, ventricular and shock electrograms. The bottom graph displays Frobenius distances of each beat from the template. All the beats have distances below the threshold level and therefore are classified as non-VT.

FIG. 5 displays a flow chart summarizing steps included in a method for discriminating supraventricular tachycardia from ventricular tachycardia/ventricular fibrillation using covariance matrices and pattern classification schemes such as Frobenius distance or support vector machines.

Figure 7A:
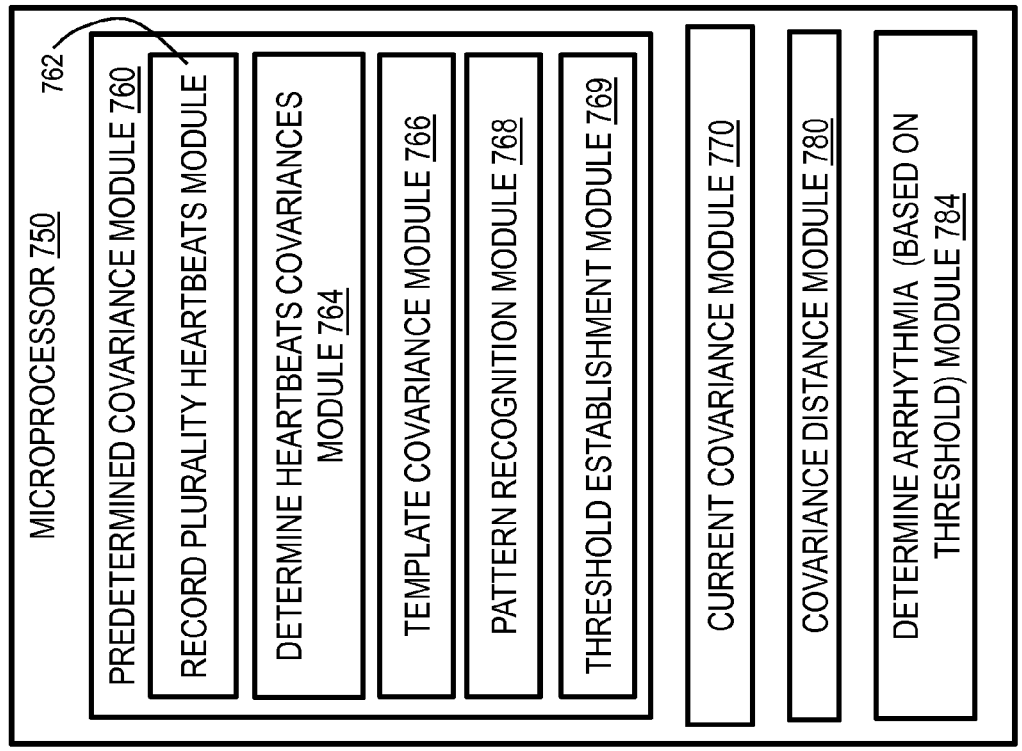
Figure 7B:
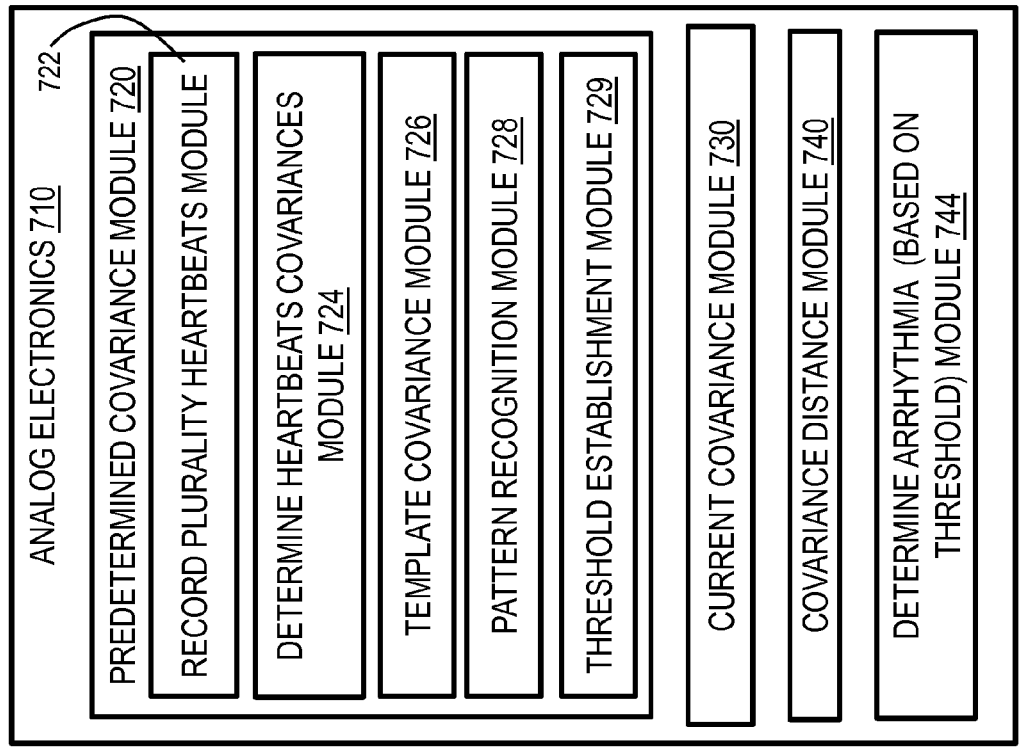

FIG. 6 displays a flow chart summarizing steps included in a method for discriminating supraventricular tachycardia from ventricular tachycardia/ventricular fibrillation using population-based template matrices and pattern classification schemes such as Frobenius distance or support vector machines. FIGS. 7A and 7B each depict an apparatus that performs one or more functions of the method described in FIG. 5 and FIG. 6.

DESCRIPTION

In the following description of the embodiments, references are made to the various embodiments in which the invention may be practiced. It is to be understood that other embodiments may be utilized, and structural and functional changes may be made without departing from the scope of the present invention.

Embodiments of the invention describe a novel, highly accurate and easy to implement, covariance-based algorithm for precise ICD rhythm classification to reduce the likelihood of false positive or false negative arrhythmia detection. Ventricular tachycardia is distinguished from supraventricular tachycardia by estimating and comparing the covariance matrices of the different heart rhythms.

Some embodiments of the invention describe the algorithm for use in an implantable medical device that provides defibrillation therapy (implantable cardioverter defibrillators, ICD), but the algorithm is also applicable to subcutaneous cardioverter defibrillators, cardiac rhythm devices (including external devices) directed toward anti-tachyarrhythmia therapy, pacing, and other cardiac rhythm devices capable of performing a combination of therapies to treat rhythm disorders.

In some embodiments of the invention, covariance matrices are calculated for one or more heartbeats. Based on different electrogram combinations, four types of covariance matrices can be formed: the electrogram combinations include atrial, ventricular or shock electrograms or a combination of two out of three, atrial+ventricular or atrial+shock or ventricular+shock. Any or all of these combinations of electrograms can be utilized.

After obtaining the covariance matrices, the Frobenius distance from a template matrix may be calculated for pattern recognition. In other embodiments of the invention, other matrix normalization methods such as support vector machines may be used to calculate distance.

If the distance is more than a predefined threshold, that beat is annotated as ventricular tachycardia (VT).

In some embodiments of the invention, the template matrix is obtained by averaging the covariance matrices of one or more normal heartbeats from a patient. Therefore, the template matrix is unique for each patient and helps to adapt to each individual patient's characteristics.

In alternative embodiments of the invention, a population-based template matrix may be developed from one or more regular heartbeats from a large group of patients (more than 100 patients).

The algorithm is applicable in both single and dual chamber ICDs and has a very high speed and low computational load. Both single and dual chamber implementations achieve the ideal 100% sensitivity for VT detection. Dual chamber implementation exhibits a slightly higher specificity since it exploits the additional information of the atrial electrogram.

In one embodiment, three types of intracardiac signals are processed in an ICD: atrial, ventricular and shock electrograms.

In another embodiment, only two types of intracardiac signals are processed in an ICD: ventricular and shock electrograms.

A wide variety of implantable cardiac monitoring and/or stimulation devices may be configured to implement an updated methodology of the present invention. A non-limiting, representative list of such devices includes cardiac monitors, pacemakers, cardioverters, defibrillators, resynchronizers, and other cardiac sensing and therapy delivery devices. These devices may be configured with a variety of electrode arrangements, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes).

The metrics that are discussed here can be implemented either in analog electronics or with low computational overhead on a microprocessor. For example, as shown in FIG. 7A, analog electronics 710 include modules for each of the steps of one or more embodiments. In the illustrated embodiment, a predetermined covariance module 720 includes a module 722 to record a plurality of heartbeats, a module 724 to determine heartbeats covariances, a module 726 to determined template covariance, a module 728 to perform pattern recognition and a module 729 to establish a pre-determined threshold. The analog electronics 710 also includes a module 730 to determine the covariance of each current heartbeat, a module 740 to determine covariance matrix distance measure and module 744 to determine whether the heartbeat is an arrhythmia (a ventricular tachycardia (VT) or supraventricular tachycardia (ST)) based on the threshold. Similarly, as shown in FIG. 7B, microprocessor 750 includes software modules for each of the steps of one or more embodiments. In the illustrated embodiment, a predetermined covariance module 760 includes a module 762 to record a plurality of heartbeats, a module 764 to determine heartbeats covariances, a module 766 to determined template covariance, a module 768 to perform pattern recognition and a module 769 to establish a pre-determined threshold. The microprocessor 750 also includes a module 770 to determine the covariance of each current heartbeat, a module 780 to determine covariance matrix distance measure and module 784 to determine whether the heartbeat is an arrhythmia (a ventricular tachycardia (VT) or supraventricular tachycardia (ST)) based on the threshold.

Tuning or training set. For each patient, a number of normal heartbeats is used as a tuning (training) set to obtain the patient's normal template and threshold level. Since the tuning set is acquired for each patient individually, normal template and threshold levels are unique for each patient and help the algorithm to adapt to each individual patient's characteristics. The training set can be acquired at any time prior to an episode or between episodes. Parameters of the learning algorithm may be adjusted by optimizing performance on a subset (validation set) of the training set, or via cross-validation.

For the determination of the threshold level, any pattern-classification and/or pattern-recognition method can be used such as the Frobenius distance, support vector machine (SVM)-based classification method and such.

Pattern recognition is a subtopic of machine learning (artificial intelligence) and aims to classify data (patterns) based either on a priori knowledge or on statistical information extracted from the patterns. The patterns to be classified are usually groups of measurements or observations, defining points in an appropriate multidimensional space; the machine learning can be supervised or unsupervised. In the present invention, the supervised learning method is utilized, since the learning of a function results from perusing training data. Supervised learning can generate models of two types. Most commonly, supervised learning generates a global model that maps input objects to desired outputs. In some cases, however, the map is implemented as a set of local models.

Covariance-based template matrices. The covariance matrices represent the second-order statistical properties of each beat per individual patient, which provide more stable quantities for classification purposes compared to the actual time series. The diagonal elements show the signal power of each electrogram, whereas non-diagonal elements explain the cross-correlation between different electrograms for each beat. A separate template matrix is established for each individual patient.

Population-based template matrices. One common template is obtained and used for all patients instead of a separate template matrix for each individual patient.

Matrix norms. In mathematics, a norm is a function that assigns a strictly positive length or size to all vectors in a vector space. A matrix norm is a natural extension of the notion of a vector norm to matrices. In this sense, a matrix norm is a norm on the vector space of all real or complex m-by-n matrices. These norms are used to measure the sizes of matrices.

Frobenius distance; Frobenius norm. The Frobenius norm is one kind of matrix norm defined as $$\|A\|_F = \sqrt{\sum_{i=1}^{m}\sum_{j=1}^{n}|a_{ij}|^2} = \sqrt{\operatorname{trace}(A^*A)} = \sqrt{\sum_{i=1}^{\min\{m,n\}}\sigma_i^2},$$

with the Frobenius distance being the Frobenius norm of the difference between two matrices ($\|A\_B\|F$).

The support vector machine (SVM)-based classification method represents a major development in pattern recognition research and is a new paradigm of learning systems. SVMs use geometrical properties to exactly calculate the optimal separating hyperplane directly from the training data. They also introduce methods to deal with nonlinearly separable cases, i.e. where no separating straight line can be found, as well as with cases in which there is noise and/or outliers in the training data. This makes SVMs a practical and effective solution for many pattern recognition and classification problems.

The most distinctive fact about SVM is that the learning task is reduced to quadratic programming by introducing Lagrange multipliers. All operations in learning and testing modes are done in SVM using kernel functions. The kernel is defined as $K(x,x_i) = \Phi^T(x_i)\Phi(x)$.

The problem of learning SVM, formulated as the task of separating learning vectors x into two classes of the destination values either $d_i = 1$ or $d_i = -1$ with maximal separation margin, is reduced to the dual maximization problem of the objective function, defined as follows:

$$Q(\alpha) = \sum_{i=1}^{P} \alpha_i - \frac{1}{2}\sum_{i=1}^{P}\sum_{j=1}^{P} \alpha_i \alpha_j d_i d_j K(x_i x_j), \quad (2)$$

with constraints:

$$\sum_{i=1}^{p} \alpha_i d_i = 0 \quad (3)$$

$$0 \leq \alpha_i \leq C,$$

where C is a user defined constant and p is the number of learning data pairs $(x_i, d_i)$. C is the regularizing parameter and determines the balance between the maximization of the margin and minimization of the classification error {Mehta & Lingayat, (2008), J Med Eng & Technol 32, pp. 206-215}.

Single-chamber versus dual-chamber ICDs. A single-chamber ICD defibrillates the ventricle and paces the ventricle, while a dual-chamber ICD defibrillates the ventricle and paces the atrium as well as the ventricle.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are herein described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

Published as well as yet unpublished work by the inventors has been described in Appendix A and is regarded as incorporated in the Detailed Description in an effort to provide those of ordinary skill in the art with a complete disclosure and description of how to make and use the subject invention.

Exemplary Algorithm Implementation

Discrimination of VT and SVT in clinical setting. Clinical study involved 77 ICD patients in the Multicenter Automatic Defibrillator Implantation Trial (MADIT II) {Moss et al. (1999), Ann Noninvasive Electrocardiol 4, pp. 83-91} as well as in the Multicenter Automatic Defibrillator Implantation Trial with Cardiac Resynchronization Therapy (MADIT-CRT) {Moss et al. (2005), Ann Noninvasive Electrocardiol 10, pp. S34-43}.

Data description. In this study we examined a total of 250 arrhythmia detection episodes obtained from 77 ICD patients. The dataset is splitted into training and testing sets. The training set consists of 70 ICD episodes from 22 patients in the Multicenter Automatic Defibrillator Implantation Trial (MADIT II) and the testing set consists of 180 ICD episodes obtained from 55 patients in the Multicenter Automatic Defibrillator Implantation Trial with Cardiac Resynchronization Therapy (MADIT-CRT).

Each episode consists of three signals: Atrial, Ventricular and Shock electrograms. The objective is to examine the ability of a novel algorithm to discriminate ventricular tachycardia from supraventricular arrhythmias. The proposed algorithm was originally developed based on 70 ICD episodes obtained from MADIT-II {Kamousi et al. (2008), 30$^{th}$ Annual International Conference of the IEEE, Aug. 20-25, 2008, pp. 5478-5481}. To further evaluate the performance of the algorithm, it was tested on 180 more ICD episodes obtained from MADIT-CRT database.

Data Preprocessing. The first step is calculating the covariance matrix of each beat as defined below:

$$R_{beat(i)} = X_{beat(i)} \cdot X_{beat(i)}^T / n_{beat(i)}$$

Where $X_{beat}(i)$ contains the time series of ith beat and $n_{beat}(i)$ represents the length of ith beat. Each episode consists of three electrograms: atrial, ventricular and shock; but in single-chamber ICDs the atrial electrogram is not available.

Therefore, to examine the performance of the algorithm for both single and dual chamber ICDs, two implementations have been tested. In the first implementation, all three available electrograms have been used to calculate the covariance matrix whereas in the second implementation, only ventricular and shock electrograms have been included. Thus for dual-chamber ICDs, $X_{beat}(i)$ is a $3 * n_{beat}(i)$ matrix consisting of all three electrograms and for single-chamber ICDs, a $2 * n_{beat}(i)$ matrix containing ventricular and shock electrograms.

The covariance matrices represent the second-order statistical properties of each beat, which provide more stable quantities for classification purposes compared to the actual time series. The diagonal elements show the signal power of each electrogram, whereas non-diagonal elements explain the cross-correlation between different electrograms for each beat.

Classification Criteria. The proposed classification rule is based on the assumption that supraventricular arrhythmias are less different from normal rhythms compared to ventricular arrhythmia. Therefore we can classify the beats based on their distances from the normal template. If the distance is more than a pre-defined threshold the beat is assumed to be a ventricular arrhythmia such as VT, whereas when the distance is less than the threshold level, the beat is either normal or supraventricular arrhythmia such as SVT.

For each patient, a number of normal heartbeats was used as a tuning set. This tuning set is used to obtain the patient's normal template and threshold level. Since the tuning set is acquired for each patient individually, normal template and threshold level are unique for each patient and help the algorithm to adapt to each individual patient's characteristics.

The normal template is obtained by averaging the covariance matrices of the beats in the tuning set:

$$R_{template} = \frac{1}{N}\sum_{i=1}^{N} R_{beat(i)}$$

where N is the total number of normal beats in the tuning set and Rbeat(i) is the covariance matrix of ith beat. In this study N was 4. Thus variability of heartbeats is compared and classified using covariance matrices.

Then for each beat, the Frobenius distance between its covariance matrix, $R_{beat(i)}$, and the normal template, $R_{template}$, is calculated as follows:

$$F(R_{beat(i)}, R_{template}) = \sqrt{tr[R_{beat(i)} - R_{template})(R_{beat(i)} - R_{template})^T]}$$

To determine the threshold level, the Frobenius distances of all the normal beats in the tuning set have been calculated from the template. Then, the threshold level is defined by multiplying the maximum distance between normal beats and template, and a constant number K:

$$\text{Threshold} = K * \max_{i=1:N}[F(R_{beat(i)}, R_{template})]$$

Figure 1:
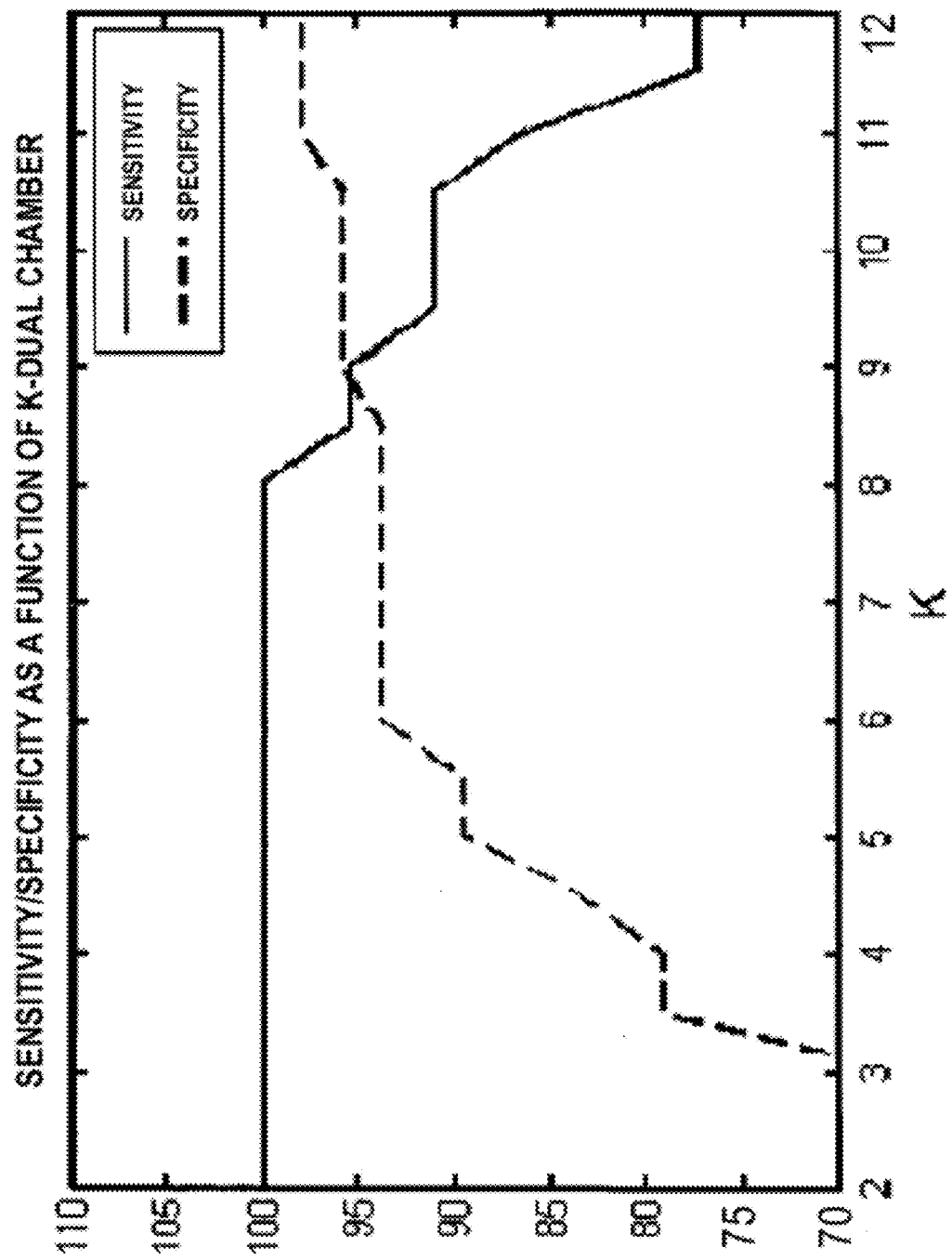
FIG. 1 illustrates the trade-off between sensitivity and specificity as constant K increases. The optimal value for dual-chamber algorithm is between 6 and 8.
Figure 2:
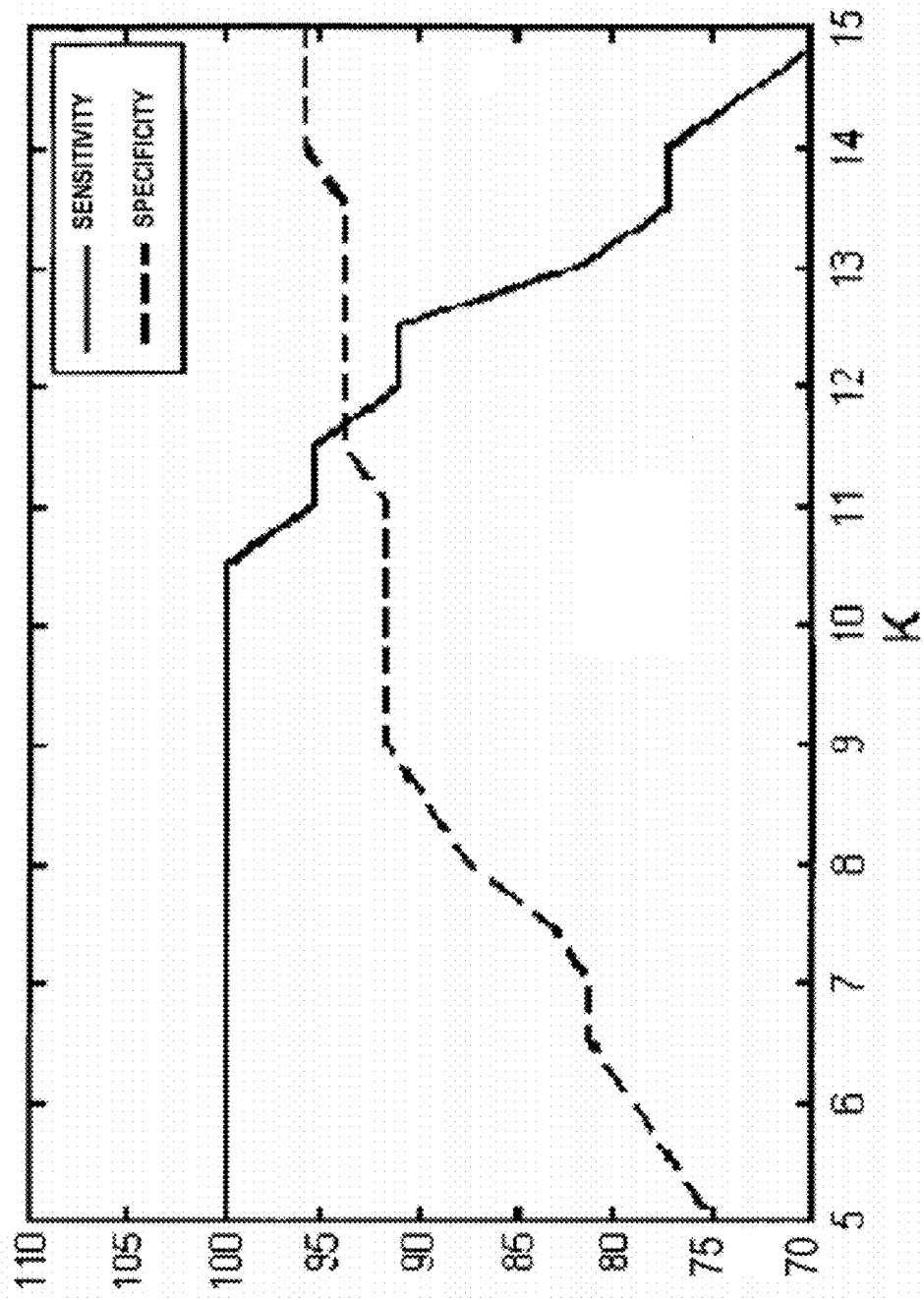
FIG. 2 illustrates the trade-off between sensitivity and specificity as constant K increases. The optimal value for single-chamber algorithm is between 9 and 11.

FIGS. 1 and 2 display the trade-off between sensitivity and specificity of dual and single chamber algorithms, as we change K. High sensitivity is ensured for lower values of K but specificity increases with K. The optimal value of K for the tuning set is between 6 and 8 (7) for dual chamber and between 9 and 11 (10) for single chamber ICDs, respectively.

Results. FIGS. 3 and 4 graphically depict examples of how VT and SVT episodes were classified. In both figures the top three graphs show the atrial, ventricular and shock electrograms. The bottom graph shows the distance of each beat from the template and the threshold level. In the VT episode (FIG. 3) the distances clearly increase beyond the threshold at the onset of VT, whereas in the SVT episode (FIG. 4) they remain below the threshold level. The proposed algorithm was originally tested on 70 therapy episodes recorded from 22 ICD patients in MADIT II. There were a total of 48 SVT and 22 VT episodes. All the episodes were annotated by cardiologists and compared with the algorithms' results.

Table 2 shows the results of applying the algorithm on all three electrograms in dual-chamber ICDs. All the VT episodes and 45 out of 48 SVT episodes were correctly classified. Consequently the sensitivity and specificity of the dual-chamber implementation are 100% and 94%, respectively {Kamousi et al. (2008), 30$^{th}$ Annual International Conference of the IEEE, Aug. 20-25, 2008, pp. 5478-5481}.

TABLE 2

| | Dual-chamber ICDs | |
| --- | --- | --- |
| | SVT | VT |
| Classified as VT | 3 | 22 |
| Classified as SVT | 45 | 0 |
| Result | Specificity: 94% | Sensitivity: 100% |

Table 3 shows the results of applying the algorithm on ventricular and shock electrograms in single-chamber ICDs. All the VT episodes and 44 out of 48 SVT episodes were correctly classified, achieving a sensitivity of 100% and specificity of 92% {Kamousi et al. (2008), 30$^{th}$ Annual International Conference of the IEEE, Aug. 20-25, 2008, pp. 5478-5481}.

TABLE 3

| | Single-chamber ICDs | |
| --- | --- | --- |
| | SVT | VT |
| Classified as VT | 4 | 22 |
| Classified as SVT | 44 | 0 |
| Result | Specificity: 92% | Sensitivity: 100% |

To further evaluate the performance of the algorithm, it was tested on 180 more ICD episodes obtained from MADIT-CRT database. There were a total of 116 episodes of ventricular and 64 episodes of supraventricular arrhythmias, among which atrial electrograms were not available for 22 VT and 9 non-VT episodes. The dual chamber algorithm could, therefore, not be tested on these 31 episodes.

Table 4 summarizes the results of applying the dual chamber algorithm on the new 149 episodes. This time sensitivity and specificity of the algorithm are 98% and 83.6%, respectively.

TABLE 4

| Dual-chamber ICDs | | |
| --- | --- | --- |
| | Non-VT | VT |
| Classified as VT | 9 | 92 |
| Classified as non-VT | 46 | 2 |
| Result | Specificity: 83.6% | Sensitivity: 98% |

The results of single chamber algorithm applied on all 180 new episodes are summarized in Table 5. It correctly classified 113 VT and 51 non-VT episodes, achieving 97.5% sensitivity and 80% specificity.

TABLE 5

| Single-chamber ICDs | | |
| --- | --- | --- |
| | Non-VT | VT |
| Classified as VT | 13 | 113 |
| Classified as non-VT | 51 | 3 |
| Result | Specificity: 80% | Sensitivity: 97.5% |

Discussion. These results suggest that the proposed algorithm may be an effective method for ICD rhythm classification and may decrease inappropriate shocks. The algorithm is applicable in both single and dual chamber ICDs and has a very high speed and low computational load. Dual chamber implementation exhibits slightly higher sensitivity and specificity since it exploits the additional information of the atrial electrogram. Further modifications such as applying more sophisticated distance measures instead of the Frobenius norm may improve the specificity while maintaining the excellent sensitivity of the algorithm.

One of the limitations in this study was the small number of normal beats available for each patient. In addition, the sinus beats close to the onset of the episodes were used as the tuning set and it is possible that the results would not be as good if the tuning set had been obtained at a different time point. In conclusion we have investigated the application of a new covariance-based algorithm for ICD rhythm classification. The results are very promising and demonstrate the potential effectiveness of this algorithm for ICD rhythm discrimination.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. Accordingly, the preceding merely illustrates the principles of the invention. It will be appreciated that those skilled in the art will be able to devise various arrangements which, although not explicitly described or shown herein, embody the principles of the invention and are included within its spirit and scope.

What is claimed is:

1. A method comprising:
   determining a current covariance matrix of a plurality of electrograms measuring each current heartbeat,
   determining a distance measure between the current covariance matrix and a predetermined covariance matrix of the plurality of electrograms measuring at least one different heartbeat; and
   determining whether the heartbeat represents ventricular tachycardia based on the distance measure.

2. A method as recited in claim 1, wherein the plurality of electrograms comprise a shock coil electrogram.

3. A method as recited in claim 1, wherein the plurality of electrograms further comprises at least one of an atrial electrogram or a ventricle electrogram.

4. A method as recited in claim 1, wherein the at least one different heartbeat comprises a heartbeat that is not a ventricular tachycardia heartbeat.

5. A method as recited in claim 1, wherein:
   the at least one different heartbeat comprises at least one ventricular tachycardia heartbeat and at least one heartbeat that is not a ventricular tachycardia heartbeat;
   the method further comprises
      determining the predetermined covariance matrix for the at least one heartbeat, of the at least one different heartbeat, which is not a ventricular tachycardia heartbeat, and
      determining a threshold distance that separates
         a ventricular tachycardia heartbeat of the at least one different heartbeat from
         a heartbeat, of the at least one different heartbeat, which is not a ventricular tachycardia heartbeat; and
   determining whether the heartbeat represents ventricular tachycardia based on the distance measure further comprises determining whether the distance measure exceeds the threshold distance.

6. A method as recited in claim 1, wherein the at least one different heartbeat comprises a heartbeat of an individual.

7. A method as recited in claim 1, wherein the at least one different heartbeat comprises a heartbeat of a plurality of different individuals.

8. An apparatus comprising:
   means for determining a current covariance matrix of a plurality of electrograms measuring each current heartbeat,
   means for determining a distance measure between the current covariance matrix and a predetermined covariance matrix of the plurality of electrograms measuring at least one different heartbeat; and
   means for determining whether the current heartbeat represents ventricular tachycardia based on the distance measure.

* * * * *